United States Patent [19]

Bundy

[11] 4,273,716

[45] Jun. 16, 1981

[54] 2-DECARBOXY-2-HYDROXYMETHYL-11A-HOMO-TXA$_2$ COMPOUNDS

[75] Inventor: Gordon L. Bundy, Portage, Mich.

[73] Assignee: The Upjohn Company, Kalamazoo, Mich.

[21] Appl. No.: 115,969

[22] Filed: Jan. 28, 1980

Related U.S. Application Data

[62] Division of Ser. No. 35,143, May 1, 1979, Pat. No. 4,218,378.

[51] Int. Cl.$^3$ .................................... C07D 309/06
[52] U.S. Cl. ........................ 260/345.9 P; 542/426; 542/429

[58] Field of Search ............. 260/345.9 R, 345.9 P; 542/426, 429

[56] References Cited

U.S. PATENT DOCUMENTS 4,052,552  10/1977  Schneider .................. 260/345.8 P

*Primary Examiner*—Nicky Chan
*Attorney, Agent, or Firm*—Robert A. Armitage

[57] ABSTRACT

The present invention provides novel thromboxane analogs and intermediates. Particularly, the present invention provides novel 2-decarboxy-2-hydroxymethyl-11a-homo-TXA$_2$ compounds.

2 Claims, No Drawings

2-DECARBOXY-2-HYDROXYMETHYL-11A-HOMO-TXA$_2$ COMPOUNDS

DESCRIPTION

CROSS REFERENCE TO RELATED APPLICATION

The present application is a division of Ser. No. 035,143, filed May 1, 1979, now U.S. Pat. No. 4,218,378.

BACKGROUND OF THE INVENTION

The present invention provides novel thromboxane analogs and intermediates. Particularly, the present invention provides novel 2-decarboxy-2-hydroxymethyl-11a-homo-TXA$_2$ compounds. The essential material constituting a disclosure of the preparation and use of the compounds described above is incorporated here by reference from the U.S. Pat. No. 4,218,378.

PRIOR ART

As indicated above, thromboxane A$_2$ is known in the art. See Hamberg, M., et al., Proceedings of the National Academy of Sciences USA 72:2994 (1975), Samuelsson, Proceedings of the National Academy of Sciences USA 71:3400-3404 (1974). Likewise, numerous analogs of thromboxane B$_2$ and their use as reproductive cycle control agents is known in the art. See U.S. Pat. No. 4,070,384, issued Jan. 24, 1978.

Other heterocyclic ring analogs of the prostaglandins include the 9α, 11α- or 11α,9α-epoxymethano-9,11-dideoxy-PGF-type compounds described in U.S. Pat. Nos. 3,950,363 and 4,028,354. Finally related azo and epoxyimino compounds are known in the art. See U.S. Pat. No. 4,112,224.

SUMMARY OF THE INVENTION

The present invention particularly provides a thromboxane analog of formula IV wherein $Y_1$ is
  (1) trans—CH=CH—,
  (2) cis—CH=CH—,
  (3) —CH$_2$CH$_2$—, or
  (4) —C≡C—,
wherein $M_1$ is α-R$_5$:β-OH, α-OH:β-R$_5$, or α-H:β-H,
wherein R$_5$ is hydrogen or methyl, and wherein $L_1$ is α-R$_3$:β-R$_4$, α-R$_4$:β-R$_3$, or a mixture of α-R$_3$:β-R$_4$ and β-R$_3$:α-R$_4$, wherein R$_3$ and R$_4$ are hydrogen, methyl, or fluoro, being the same or different, with the proviso that one of R$_3$ and R$_4$ is fluoro only when the other is hydrogen or fluoro, or wherein —C(M$_1$)—C(L$_1$)— is trans—CH=CH—;
wherein $Z_1$ is
  (1) cis—CH=CH—CH$_2$—(CH$_2$)$_g$—CH$_2$—,
  (2) cis—CH=CH—CH$_2$—(CH$_2$)$_g$—CF$_2$—,
  (3) cis—CH$_2$—CH=CH—(CH$_2$)$_g$—CH$_2$—,
  (4) —(CH$_2$)$_3$—(CH$_2$)$_g$—CH$_2$—,
  (5) —(CH$_2$)$_3$—(CH$_2$)$_g$—CF$_2$—,
  (6) —CH$_2$—O—CH$_2$—(CH$_2$)$_g$—CH$_2$—,
  (7) —(CH$_2$)$_2$—O—(CH$_2$)$_g$—CH$_2$—, or
  (8) trans—CH$_2$—(CH$_2$)$_g$—CH$_2$—CH=CH—;
  (9) —(m-Ph)—O—(CH$_2$)$_g$—, or
  (10) —(m-Ph)—CH$_2$—(CH$_2$)$_g$—,
wherein g is one, 2, or 3 and -(m-Ph)— is meta-phenylene; and
wherein R$_7$ is
  (1) —(CH$_2$)$_m$—CH$_3$, wherein m is an integer from one to 5, inclusive;
  (2) phenoxy;
  (3) phenoxy substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
  (4) phenyl;
  (5) phenyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
  (6) phenylmethyl, phenylethyl, or phenylpropyl; or,
  (7) phenylmethyl, phenylethyl, or phenylpropyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl; with the proviso that R$_7$ is phenoxy or substituted phenoxy, only when R$_3$ and R$_4$ are hydrogen or methyl, being the same or different.

DESCRIPTION OF THE PREFERRED EMBODIMENTS

The specific embodiments of the present invention include:
2-decarboxy-2-hydroxymethyl-11a-methano-TXA$_2$
2-decarboxy-2-hydroxymethyl-11a-methano-15-deoxy-TXA$_2$.

The novel 11a-methano-TXA analogs of the present invention are all highly active as inhibitors of thromboxane synthetase and accordingly are useful for anti-inflammatory, anti-asthma and anti-thrombotic indications.

I claim:
1. A thromboxane analog of formula IV wherein $Y_1$ is
  (1) trans-CH=CH—,
  (2) cis—CH=CH—,
  (3) —CH$_2$CH$_2$—, or
  (4) —C≡C—,
wherein $M_1$ is α—R$_5$:β—OH, α—OH:β-R$_5$, or α—H:β-H,
wherein R$_5$ is hydrogen or methyl, and wherein $L_1$ is α-R$_3$:β-R$_4$, α-R$_4$:β-R$_3$, or a mixture of α-R$_3$:β-R$_4$ and β-R$_3$:α-R$_4$, wherein R$_3$ and R$_4$ are hydrogen, methyl, or fluoro, being the same or different, with the proviso that one of R$_3$ and R$_4$ is fluoro only when the other is hydrogen or fluoro, or wherein —C(M$_1$)—C(L$_1$)— is trans—CH=CH—;

wherein $Z_1$ is
- (1) cis-13 CH=CH—CH$_2$—(CH$_2$)$_g$—CH$_2$—,
- (2) cis—CH=CH—CH$_2$—(CH$_2$)$_g$—CF$_2$—,
- (3) cis—CH$_2$—CH=CH—(CH$_2$)$_g$—CH$_2$—,
- (4) —(CH$_2$)$_3$—(CH$_2$)$_g$—CH$_2$—,
- (5) —(CH$_2$)$_3$—(CH$_2$)$_g$—CF$_2$—,
- (6) —CH$_2$—O—CH$_2$—(CH$_2$)$_g$—CH$_2$—,
- (7) —(CH$_2$)$_2$—O—(CH$_2$)$_g$—CH$_2$—, or
- (8) trans—CH$_2$—(CH$_2$)$_g$—CH$_2$—CH=CH—;
- (9) —(m-Ph)—O—(CH$_2$)$_g$—, or
- (10) —(m-Ph)—CH$_2$—(CH$_2$)$_g$—, wherein g is one, 2, or 3 and —(m—Ph)— is meta-phenylene; and wherein $R_7$ is
- (1) —(CH$_2$)$_m$—CH$_3$, wherein m is an integer from one to 5, inclusive;
- (2) phenoxy;
- (3) phenoxy substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
- (4) phenyl;
- (5) phenyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
- (6) phenylmethyl, phenylethyl, or phenylpropyl; or
- (7) phenylmethyl, phenylethyl, or phenylpropyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl; with the proviso that $R_7$ is phenoxy or substituted phenoxy, only when $R_3$ and $R_4$ are hydrogen or methyl, being the same or different.

2. 2-Decarboxy-2-hydroxymethyl-11a-methano-TXA$_2$, a compound according to claim 1.

* * * * *